United States Patent [19]

Diamond

[11] 4,139,007
[45] Feb. 13, 1979

[54] METHOD AND APPARATUS FOR CONTRACEPTION

[76] Inventor: Harvey Diamond, c/o Saul Epstein, 1880 Century Park East, Suite 500, Los Angeles, Calif. 90067

[21] Appl. No.: 725,005

[22] Filed: Sep. 20, 1976

[51] Int. Cl.² ............................................. A61B 19/00
[52] U.S. Cl. ................................. 128/138 R; 128/79; 128/DIG. 25
[58] Field of Search ................. 128/79, 346, 325, 327, 128/138, DIG. 25

[56] References Cited

U.S. PATENT DOCUMENTS

| 938,808 | 11/1909 | Yount | 128/79 |
| 2,581,114 | 1/1952 | Larson | 128/79 |
| 2,756,753 | 7/1956 | Means | 128/346 |
| 3,678,935 | 7/1972 | Bronstein | 128/325 |
| 3,705,580 | 12/1972 | Gauthier | 128/79 |

Primary Examiner—Lawrence W. Trapp

[57] ABSTRACT

A method of male contraception utilizing external pressure applied to the underside of the penis at the base thereof to close the urethral canal and thereby prevent the escape of semen. Apparatus comprises a pressure pad which applies a concentrated force on the canal and is held in place by a strap member around the penis.

2 Claims, 7 Drawing Figures

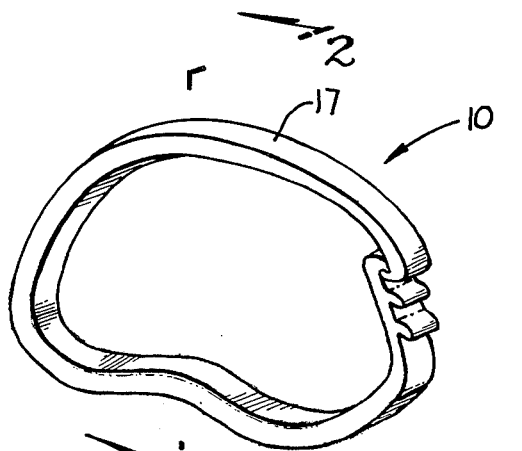
Fig. 1
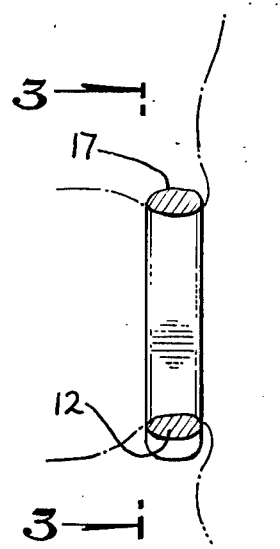
Fig. 2
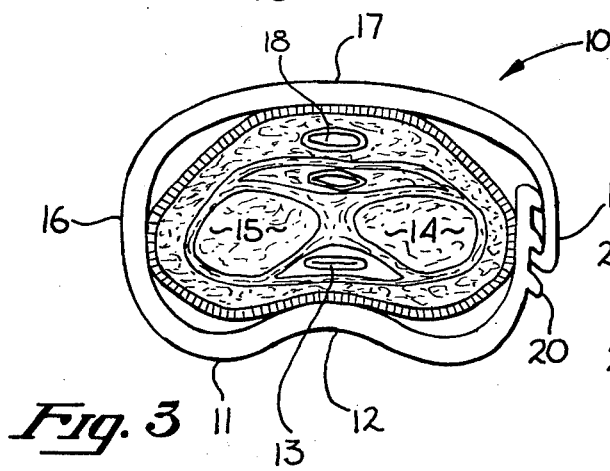
Fig. 3
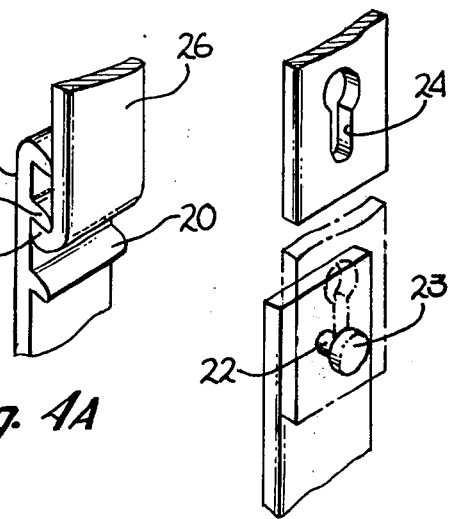
Fig. 4A
Fig. 4B
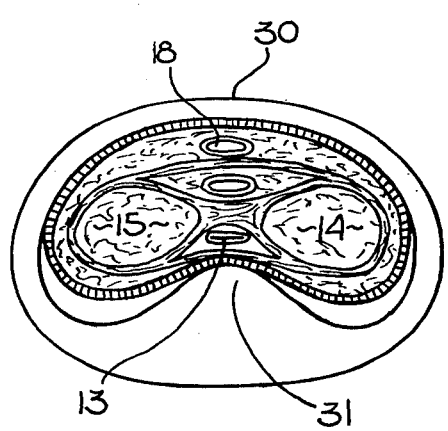
Fig. 5
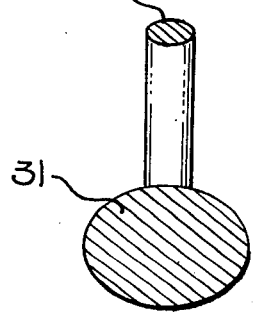
Fig. 6

METHOD AND APPARATUS FOR CONTRACEPTION

BACKGROUND OF THE INVENTION

1. Field of the Invention

This invention relates to the field of methods and apparatus for contraception and more particularly to a method and devices for male contraception.

2. Prior Art

The traditional male contraceptive device is the condom. While generally effective, condoms are not popular with men because of their well known effect of reducing feeling and consequent enjoyment of the sexual act. For this and other reasons, female contraception has become popular in recent years and the "pill" and intrauterine devices are widely used. Recently both of these methods of contraception have come under attack for their possible adverse health effects on the users. There remains a pressing need, particularly among the poorer nations of the world, for an inexpensive and safe contraceptive method and device which is both simple to use and effective. The present invention is intended to fulfill this need.

There are a number of devices in the prior art which apply pressure to the dorsal vein of the penis and which restrict blood flow from the penis and thereby prolong erection. See, e.g., U.S. Pat. No. 3,794,020. There are also devices for applying pressure to the urethra so as to retain urethral medicants or to prevent enurisis. See U.S. Pat. No. 1,748,227 and No. 3,147,754.

None of the devices in the prior art, however, apply pressure to the urethra during erection so as to close it off and prevent semen leakage.

SUMMARY OF THE INVENTION

The method and apparatus of the present invention provides the means for effective contraception without the dangers inherent in female chemical or mechanical methods or the reduction in enjoyment which accompanies the use of prior art male contraceptive devices. The invented method is simple, but prior art workers have avoided and/or overlooked the possibility, perhaps because it was believed that the method would interfere with enjoyment of the copulative act or would not be effective. It turns out, however, that the method does not at all interfere with full enjoyment, and if anything, heightens the feelings obtained, and is extremely effective.

As can be ascertained by reference to any elementary text on the subject, semen is ejaculated during orgasm through the penile urethra which is located adjacent to the bottom surface of the penis. By simply pressing on the lower surface of the penis at its base, the urethra can be closed effectively, preventing semen from ejaculating into the female vagina. Surprisingly, blocking the urethral passage during erection and orgasm has no significant effect on the orgasmic feeling and yet is effective in preventing the passage of semen.

DESCRIPTION OF THE FIGURES

FIG. 1 is a perspective view of a first embodiment of the invented apparatus.

FIG. 2 is a side view of the apparatus of FIG. 1.

FIG. 3 is an end view of the apparatus of FIG. 1 in place, the penis shown in cross section. This view is taken at plane 3—3 of FIG. 2.

FIG. 4A is an enlarged perspective view of the catch portion of the apparatus of FIG. 1.

FIG. 4B is an enlarged view of an alternate catch which might be used with the apparatus of FIG. 1.

FIG. 5 is an end view of a second embodiment of the invented apparatus in place, the penis shown in cross section.

FIG. 6 is a cross sectional view of the apparatus of FIG. 5 taken at plane 6—6 of FIG. 5.

DETAILED DESCRIPTION OF THE INVENTION

As previously stated, the method of the present invention is extremely simple even though it surprisingly does not interfere with the enjoyment of the copulative act and is effective. The method comprises merely pressing against the underside of the erect penis at or adjacent to its base during coitus with sufficient pressure to close the urethral canal and thereby prevent leakage of semen. The pressure is maintained until the penis is withdrawn from the vagina and then released. The ejaculate flows out of the penis when the pressure is removed, but since the penis is no longer in the vagina, no conception results. The ejaculate can be released immediately after coitus and it is probably desirable to do so although what, if any, effect there might be from relatively long retention is not known. Short term retention is not uncomfortable nor does there seem to be any deleterious effect.

A first embodiment of an appliance for practicing the present invention is illustrated in FIGS. 1 through 4 wherein can be seen a formed band 10 which can be fabricated from any suitable material such as metal or hard plastic. While there are no critical dimensions involved in the device, a width of three-eights to one-half inch results in an effective and comfortable appliance. A convenient thickness is one-sixteenth inch. The above dimensions are given for the purpose of illustration only and are not intended to be limiting.

The bottom portion 11 of the band contains an inwardly extending hump 12 whose purpose is to bear against the underside of the penis between the corpus cavernosa, applying the pressure required to close the urethra 13. It takes surprisingly little pressure to close the canal but it is necessary that the pressure be concentrated since the corpus cavernosa 14 and 15 are very hard during erection and unless force is applied between them, the canal 13 may not be closed or, if sufficient force is applied to close the canal, discomfort may ensue. The band is continuous from bottom portion 11 around one side 16 to top portion 17 which bears on the top of the penis. If desired, top portion 17 may have a depression (not shown) similar to the hump 12 in the bottom portion for the purpose of restricting blood flow in the superficial dorsal vein 18 which reputedly has therapeutic value for maintaining the erections of impotent males.

The band is split on the side opposite side 16 and a catch 19 provided to hold the band closed when in use. Many forms of catch are of course known to the prior art and the particular form disclosed herein is merely illustrative of the possibilities. The catch as shown in FIG. 4A is adjustable but need not be since a single size appliance will operate satisfactorily over a substantial range of organ sizes. The catch shown in FIG. 4A is comprised of a series of depending ribs 20 extending from the exterior surface of the lower side portion 25 of the appliance. The upper side portion 26 of the appliance carries a mating upturned rib 21 which will fit into the spaces between any of the ribs 20 as needed to adjust the size of the appliance.

FIG. 4B illustrates a second type of catch which could be used. The lower side portion 25 of the appliance carries an outwardly extending pin 22 which has a head 23 thereon. A mating opening 24 in the upper side portion 26 snaps over pin 22 and head 23 prevents disengagement due to lateral motion.

It should be noted that for optimum comfort the penis should not fill the entire opening in the appliance. It is preferable that the size of the appliance relative to the penis be as shown in FIG. 3 where the penis is shown just touching sides 16 and 25 without exerting any pressure thereon. If the appliance is too large, side to side, there is a possibility that the hump 12 can move so that the urethra 13 is not kept closed; on the other hand if the appliance is too small, discomfort may ensue.

A second embodiment of an appliance in accordance with the present invention is illustrated in FIGS. 5, 6 and 7 and is made of a suitable elastomer such as neoprene or flexible plastic. This embodiment is a single molded part and is comprised of a strap portion 30 which extends over the top of the penis and is connected to the ends of the pressure pad 31. The pressure pad 31 is made sufficiently stiff so that it does not bend substantially when in place on an erect penis, and is shaped so that pressure can be brought to bear on the urethra without unduely pressing on the corpus cavernosa. The length of pad 31 is slightly more than the cross sectional width of the penis so that when in place the penis does not fill the entire space. This embodiment is most easily put on over a flaccid penis but it can be rolled or slipped over an erect one, if desired.

What is claimed is:

1. A male contraceptive appliance which comprises:
   a stiff pressure pad for applying pressure to a male urethra said pad being shaped to concentrate pressure on said urethra; and
   a strap for bearing on the top of the penis and for holding said pressure pad against the underside of said penis whereby said urethra will be closed during coitus, said strap not applying pressure to the sides of the penis, and the area of said strap being such as to apply substantially less unit pressure to the top of said penis with respect to the pressure being applied in the region of said urethra, said pressure pad and said strap being a single molded piece.

2. A method of male contraception which comprises encircling the base of the penis during coitus with a single piece deformable noncircular ring like appliance, said appliance being deformable to position on an erect penis, whereby the urethral canal is compressively closed, concentrated pressure being applied in the region of the urethra but pressure in regions away from the urethra being substantially less than the pressure in the region of the urethra, and the cross section of the penis being less than the opening in said appliance whereby the penis does not completely fill said opening.

* * * * *